US00PP13684P29

(12) United States Plant Patent
Heims

(10) Patent No.: US PP13,684 P2
(45) Date of Patent: Mar. 25, 2003

(54) TIARELLA PLANT NAMED 'BLACK SNOWFLAKE'

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 10/079,437

(22) Filed: Feb. 19, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette Para
(74) *Attorney, Agent, or Firm*—Klarquist Sparkman LLP

(57) ABSTRACT

A new and distinct hybrid of Tiarella characterized a distinct leaf form and coloration.

1 Drawing Sheet

Botanical classification: Tiarella hybrid.
Variety denomination: 'Black Snowflake'.

BACKGROUND OF THE INVENTION

The present invention relates to a new and distinct cultivar of a hardy herbaceous perennial of the genus Tiarella, and known by the cultivar name 'Black Snowflake'. The genus Tiarella is a member of the family Saxifragaceae.

The new cultivar originated as a cross between unknown parents. This new Tiarella was one of many seedlings grown from select interspecific hybrids and species that were mass pollinated in the greenhouse in Canby, Oreg. From observation of the characteristics exhibited by the instant plant, it is most likely an interspecific hybrid. As such no species designations are given.

SUMMARY OF THE INVENTION

This plant is characterized by the following:

1. Distinct, deeply palmately lobed leaves.
2. Striking, dark coloration on the leaf veins and continuing almost to the margins.
3. Slightly stoloniferous habit.
4. Early bloom time and good reblooming.
5. Excellent vigor.
6. Good winter color.

The new variety has been reproduced only by asexual propagation (division and micropropagation). Each of the progeny exhibits identical characteristics to the original plant. Asexual propagation by division and standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The FIGURE is of Tiarella 'Black Snowflake' still in bloom in a pot in July in Canby, Oreg.

DETAILED PLANT DESCRIPTION

The following is a detailed description of the new Tiarella hybrid based on observations of two-and-a-half-year-old plants grown in three-gallon pots in Canby, Oreg. The color descriptions are all based on The Royal Horticultural Society Colour Chart.

Botanical classification: Tiarella hybrid.
Cultivar name: 'Black Snowflake'.
Plant:
- *Type.*—Herbaceous perennial, sometimes stoloniferous.
- *Hardiness.*'USDA Zones 5 to 9.
- *Form.*—Basal clump.
- *Size.*—62 cm. wide and 18 cm. high; new spring leaves are upright raising the spring height to 24 cm.
- *Stolons.*—Spread 0 to 11 cm per year.

Foliage:
- *Type.*—Simple.
- *Arrangement.*—Rosette.
- *Shape.*—Ovate in outline. Maple leaf shape.
- *Lobing.*—9 main lobes, palmatifid, with the terminal lobe the longest, often parted to the vein, lobes have 1 to 6 secondary lobes.
- *Margins.*—Slightly undulate.
- *Venation.*—Palmate.
- *Apex.*—Mucronulate to acute.
- *Base.*—Cordate, usually overlapping.
- *Length.*—Variable, 7 to 11 cm.
- *Width.*—Variable, 6 to 10 cm.
- *Texture.*—Rough.
- *Aspect.*—Matte.
- *Surface.*—Hirsute top and bottom.
- *Petiole length.*—10 to 20 cm.
- *Petiole texture.*—Strongly pubescent.
- *Petiole color.*—In spring — Greyed Orange 177A on bottom ¾ and Yellow Green 146C on the top ¼. In summer — Brown 200B with sun side more maroon.
- *Leaf color.*—The outside half of the leaf is deep green, Green 138A, with a dark maroon pattern of Greyed Purple 187A along the veins spreading about ¾ or more toward the margin. In winter the leaf edges are green, Green 137A and the rest is a black maroon color, between Black 202A and Greyed Purple 187A.

Inflorescence:

*Type.*—Raceme or panicle.

*Flower number.*—70 blooms per raceme and about 70 racemes blooming in the first flush, the racemes sometimes once to twice branching, extending the bloom time.

*Bloom period.*—April to May with sporadic rebloom throughout the summer and fall.

*Peduncle.*—With one or two green or green with dark-veined cauline leaves. Height — 42 cm. Width — 2.5 mm. at the widest point. Color — Yellow green 146B overall, darker at the base and the tip (Greyed Orange 177A). Texture — Hispid.

*Pedicel.*—Length — 0.8 cm. Texture — Puberulent. Color — Greyed Orange 177B.

Flower bud:

*Size.*—0.3 cm.

*Description.*—Puberulent, downfacing, campanulate when opening.

*Color.*—Cream, Greyed Yellow 162D.

Flower:

*Type.*—Perfect, actinomorphic, sepals petaloid.

*Shape.*—Rotate, with stamens extruded.

*Petal and sepal number.*—5 petals, 5 fused sepals.

*Flower size.*—0.9 cm. wide and 0.5 cm. deep including stamens.

*Petal shape.*—Elliptic and sometimes laciniate with a clawed base.

*Petal size.*—0.4 cm long and 0.1 cm. wide.

*Petal color.*—White 155D.

*Calyx.*—Petaloid, parted almost to the base.

*Calyx size.*—0.35 cm. wide and 0.1 cm. deep.

*Calyx color.*—White 155D.

*Stamens.*—10, conspicuously exerted.

*Filaments.*—White 155A.

*Anthers undehisced.*—Red Orange 35B.

*Pollen color.*—Orange Red 34B.

*Pistil.*—White 155A.

*Fragrance.*—*None.*

Fruit:

*Type.*—A one-celled capsule, beak-like, composed of two unequal parts.

*Size.*—0.4 cm long.

*Color.*—Grey-Brown 199B.

Seeds:

*Color.*—Black 202A.

*Shape.*—Minute, linear.

*Fertility.*—Fertile.

Disease resistance: This new hybrid shows good mildew tolerance, the main problem for Tiarella.

COMPARISONS WITH SIMILAR TIARELLA

Compared with Tiarella 'Mint Chocolate' (U.S. Plant Pat. No. 11,379), Tiarella 'Black Snowflake' has white flowers rather than pink. In addition is has more leaf lobes.

Compared with Tiarella 'Ninja' (U.S. Plant Pat. No. 11,168), Tiarella 'Black Snowflake' has more leaf lobes and a darker leaf pattern.

Compared to Tiarella 'Spanish Cross' (U.S. Plant Pat. No. 11,345), Tiarella 'Black Snowflake' has bigger leaves with a darker pattern, is more lobed, and has lighter flower buds.

Compared to Tiarella 'Iron Butterfly' (U.S. Plant patent application Ser. No. 09/324,627), Tiarella 'Black Snowflake' has a darker pattern, a stoloniferous rather than clumping habit, and cream rather than pink flower buds.

I claim:

1. A new and distinct hybrid of Tiarella plant substantially as shown and described, characterized by a distinct leaf form and coloration.

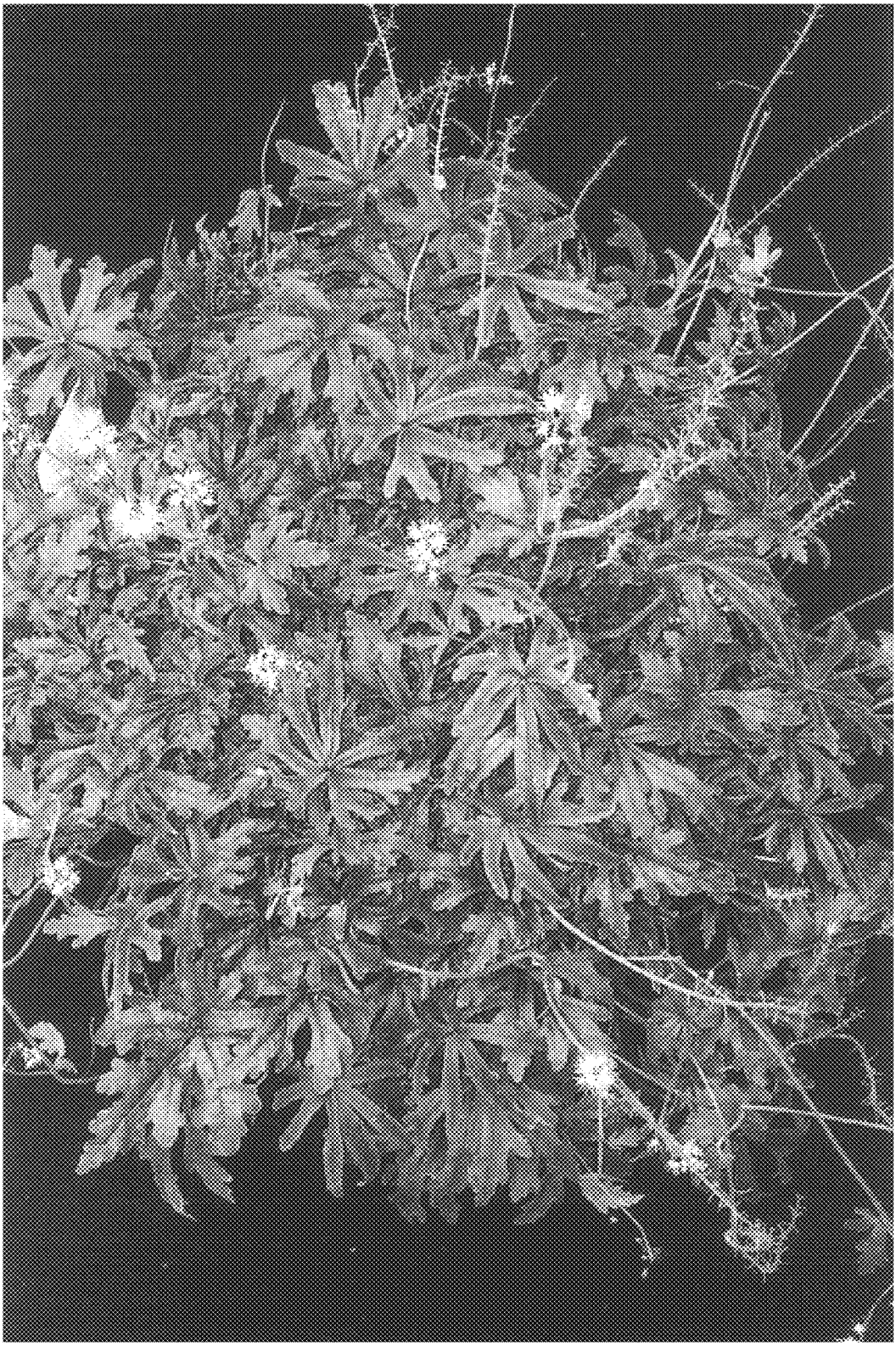

* * * * *